(12) United States Patent
Mukhopadhyay et al.

(10) Patent No.: US 6,977,316 B1
(45) Date of Patent: Dec. 20, 2005

(54) DIRECT ONE-STEP SYNTHESIS OF TRIFLUOROMETHYL IODIDE

(75) Inventors: Sudip Mukhopadhyay, Buffalo, NY (US); HsuehSung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 21 days.

(21) Appl. No.: 11/007,568

(22) Filed: Dec. 8, 2004

(51) Int. Cl.$^7$ ............................................. C07C 19/16
(52) U.S. Cl. ..................... 570/174; 570/101; 570/123; 570/162; 570/246; 570/247; 570/248; 570/250; 570/252; 570/254
(58) Field of Search .............................. 570/101, 123, 570/162, 174, 246, 247, 248, 250, 252, 253, 570/254

(56) References Cited

U.S. PATENT DOCUMENTS

| | | | |
|---|---|---|---|
| 4,794,200 A | 12/1988 | Tordeux et al. | ............. 570/170 |
| 5,892,136 A | 4/1999 | Nagasaki et al. | ............. 570/174 |

FOREIGN PATENT DOCUMENTS

| | | |
|---|---|---|
| EP | 0266281 A1 | 9/1987 |

OTHER PUBLICATIONS

European Search Report, dated Jan. 5, 1998, 1 page.
De-Bao Su et al., *Simple, Novel Method for the Preparation of Trifluoromethyl Iodide and Diiododifluoromethane,* Shanghai Institute of Organic Chemistry, Academia Sinica.
Naumann et al, *Preparation and Properties of ZnBr($CF_3$)• 2L—A Convenient Route for the Preparation of $CF_3I$.,* Institute for Anorganische Chemie, 1994.
Chiriac et al., *Obtinerea si purfiicarea $CF_3I$, $CF_3Br$, $CF_3D$, pentru separari izotopice laser,* Revista de Chimie, 1982.
Nagasaki et al., *The Development of a Novel Catalytic Technology for $CF_3I$ Manufacture,* Halon Options Technical Working Conference, May 2000.
Glass et al., *Gas Phase Combustion Suppression of Various Fuels by $CF_3I$,* Halon Options Technical Working Conference, Apr. 1999.
Dhooge et al., *Low Environmental Impact, High Performance Foam Blowing Agents Based on Iodofluorcarbons,* Environmental and Technology Education Center.
*F-Tech's Position Towards Commercialization of its Novel $CF_3I$ Technology,* Halon Options Technical Working Conference, May 2000.
Abstract of DE 1805457.
Abstract of JP 52068110.
Abstract, *Study on a Novel Catalytic Reaction and its Mechanism for $CF_3I$ Synthesis.*
Abstract, *A Simple, Novel Method for the Preparation of Trifluoromethyl Iodide and Diiododifluoromethane.*
Abstract, *Synthesis of $CF_3I$ by Direct Iodination of $CF_3COOH$ on Solid Catalyst.*
Abstract, *Synthesis and Purification of Iodotrifluoromethane, Bromotrifluormethane, Trifluormethane-d1 for Laser Isotope Separation.*

Primary Examiner—Elvis O. Price
Assistant Examiner—Lansana Nyalley
(74) Attorney, Agent, or Firm—Colleen D. Szuch

(57) ABSTRACT

A catalytic one-step process for the production of $CF_3I$ by reacting, preferably in the presence of a source of oxygen, a source of iodine with a reactant of the formula:

$$CF_3R$$

where R is —SH, —S—S—$CF_3$, —S-phenyl, or —S—Si—$(CH_3)_3$. The catalyst may be a metal salt such as salts of Cu, Hg, Pt, Pd, Co, Mn, Rh, Ni, V, TI, Ba, Cs, Ca, K and Ge and mixtures thereof, preferably on a support such as MgO, BaO and CaO, $BaCO_3$, $CsNO_3$, Ba $(NO_3)_2$, activated carbon, basic alumina, and $ZrO_2$.

10 Claims, No Drawings

DIRECT ONE-STEP SYNTHESIS OF TRIFLUOROMETHYL IODIDE

FIELD OF THE INVENTION

This invention relates to a direct one-step method for the synthesis of trifluoromethyl iodide, $CF_3I$, by reaction of iodine with various perfluoromethyl compounds.

BACKGROUND TO THE INVENTION

Mechanical refrigeration systems, and related heat transfer devices such as heat pumps and air conditioners, using refrigerant liquids are well known in the art for industrial, commercial and domestic uses. Chlorofluorocarbons (CFCs) were developed in the 1930s as refrigerants for such systems. However, since the 1980s the effect of CFCs on the stratospheric ozone layer has become the focus of much attention. In 1987 a number of governments signed the Montreal Protocol to protect the global environment setting forth a timetable for phasing out the CFC products. CFC's were replaced with more environmentally acceptable materials that contain hydrogen or hydrochlorofluorocarbons (HCFC's). Subsequent amendments to the Montreal protocol accelerated the phase-out of these CFCs and also scheduled the phase-out of HCFCs. Additionally, it is expected that the European Union member states will shortly recommend banning the use of materials that have a Global Warming Potential (GWP) of 50 or more. Thus, there is a requirement for a non-flammable, non-toxic alternative to replace these CFCs and HCFCs. In response to such demand industry has developed a number of hydrofluorocarbons (HFCs), which have a zero or near zero ozone depletion potential.

$CF_3I$ is a non-toxic, non-flammable, low global warming potential molecule with almost zero ozone depletion potential. Also the life cycle of the $CF_3I$ in the atmosphere is only a couple of days. Thus, there is incentive to synthesize this molecule in a low-cost route for using it as a refrigerant with or without the presence of a known or existing refrigerants. The $CF_3I$ is also useful a foam blowing agent and can be used to replace more environmentally damaging foam blowing agent previously employed in the production of polymeric foams.

Prior to this invention the methods known for the production of $CF_3I$ have involved or required one or more of expensive and/or not readily available reactants, multi-steps processes, processes with low selectivity for $CF_3I$, processes with low yields, and processes limited to lab scale production quantities. The following are exemplary of such prior art processes.

In the article "Study on a novel catalytic reaction and its mechanism for $CF_3I$ synthesis", Nagasaki, Noritaka et al., Catalysis Today (2004), 88(3–4), 121–126, a vapor phase production process has synthesized $CF_3I$ by the reaction between $CHF_3$ with $I_2$ in the presence of a catalyst including alkali metal salts, which are supported on an activated carbon carrier. A consideration of the reaction mechanism suggests that the reaction proceeds via $CF_2$ carbenes formed on the catalyst surface as intermediates, followed by carbene disproportionation to $CF_3$ radicals, followed by reaction with $I_2$ to give $CF_3I$.

It has been claimed in JP 52068110 that $CF_3I$ is prepared in high yield by vapor-phase reaction of Freon 23 with iodine in the presence of alkali or alkaline earth metal salts. Thus, 200 mL/min Freon 23 is introduced to iodine, the resulting gaseous mixture of Freon 23 and iodine (iodine/Freon=2.2 molar) is passed over 800 mL active carbon containing 7.5% KF for 10 h at 500° C. to give 57.8% $CF_3I$.

In DE 1805457 $CF_3I$ and $C_2F_5I$ have been prepared from the corresponding bromides and KI without solvents. Thus, 0.3 mole $CF_3Br$ are passed through a layer of 3 mole KI of 6–8 micron particle size at 500° C. to give 15% $CF_3I$, 0.3% $C_2F_6$, and 85% $CF_3Br$, which is then recycled.

$CF_3Br$ have also been used as a starting material to synthesize $CF_3I$ in a multi-step reaction protocol in "Preparation and properties of ZnBr(CF3) 2 L—a convenient route for the preparation of $CF_3I$", Naumann, Dieter; et al, Journal of Fluorine Chemistry (1994), 67(1), 91–3. $ZnBr(CF_3)$ 2 L (L=DMF, MeCN) is prepared by the reactions of $CF_3Br$ with elemental Zn in better than 60% yield. The reaction of $ZnBr(CF3)_2DMF$ with Iodine monochloride in DMF solution yields pure $CF_3I$ in better than 70% yield.

In a similar approach, disclosed in EP 266821 and U.S. Pat. No. 4,794,200, $CF_3I$ is prepared from $CF_3Br$ by contact with a metal or an alkali metal dithionite and $SO_2$ in solution followed by filtration and treatment with iodine in a carboxylic or sulfonic acid. Thus, Zn, NaOH, and $SO_2$ in DMF in a Parr app. were pressurized with 3.7 bar CF3Br and the mixture. stirred 2 h whereupon the product was heated at 120° C. over 9 h with iodine in HOAc during which $CF_3I$ (32%) was generated and recovered.

A direct synthesis of $CF_3I$ by direct iodination of $CF_3CO_2H$ with iodine has been claimed using a flow reactor over various salt-impregnated catalysts, such as copper iodide on activated carbon, in "Synthesis of $CF_3I$ by direct iodination of $CF_3COOH$ on solid catalyst", Lee, Kyong-Hwan et al, Hwahak Konghak (2001), 39(2), 144–149. In this experiment, the effects of support types, salt types and salt contents for the manufactured catalysts and also those of reaction conditions such as reaction temperature, contact time and feeding mole ratio of reactant are tested. It has been reported that a longer contact time led to the higher yield of $CF_3I$. The optimized reaction conditions were above 1 of $I_2/CF_3COOH$ mole ratio and about 400° C. of reaction temp. Active-carbon as a support shows better performance than alumina. For the salt impregnated on support, the best results of both salt content and salt type are 7.5 wt. percentages and CuI type, respectively. In the reaction conditions in this article, the catalyst was readily deactivated.

In "A simple, novel method for the preparation of trifluoromethyl iodide and diiododifluoromethane", Su, Debao et al., Journal of the Chemical Society, Chemical Communications (1992), (11), 807–8, $CF_3I$ has been synthesized in 70–80% yields by treatment of $XCF_2CO_2Me$ (X=Cl or Br) with iodine in the presence of potassium fluoride and copper (I) iodide. If KI is used instead of KF under similar conditions, $CF_2I_2$ is obtained in 50–60% yields with traces of MeI present. Reaction of $BrCF_2CO_2K$ with KI and $I_2$ in the presence of CuI gave $CF_2I_2$ in 50–60% yield without traces of MeI.

In a different approach, in "Synthesis and purification of iodotrifluoromethane, bromotrifluoromethane, trifluoromethane-d1 for laser isotope separation". Chiriac, Maria et al., Revistade Chimie (Bucharest, Romania) (1982), 33(11), 1018–20, $CF_3I$ of 99.9% purity have been prepared with yield >80% from Ag-trifluoroacetate.

There is, therefore, a need for an alternative, fairly simple and inexpensive process, and preferably a one-step process, for the production of $CF_3I$ that does not require expensive and/or not readily available reactants, and in which the process can be commercially adapted.

SUMMARY OF THE INVENTION

A catalytic one-step process for the production of $CF_3I$ using relatively inexpensive reactant feedstocks has been discovered. The process comprises reacting, preferably in the presence of a source of oxygen, a source of iodine selected from iodine, hydrogen iodide or iodine monochloride (ICI) with a reactant selected from those of the formula:

$CF_3R$ where R is selected from the group consisting of —SH, —S—S—$CF_3$, —S-phenyl, and —S—Si—$(CH_3)_3$ in the presence of a catalyst preferably consisting of a metal salt such as salts of Cu, Hg, Pt, Pd, Co, Mn, Rh, Ni, V, TI, Ba, Cs, Ca, K and Ge and mixtures thereof.

DETAILED DESCRIPTION OF INVENTION

A catalytic one-step process for the production of $CF_3I$ comprises reacting, preferably in the presence of a source of oxygen, a source of iodine selected from iodine, hydrogen iodide or iodine monochloride with a reactant selected from those of the formula:

$CF_3R$ where R is selected from the group consisting of —SH, —S—S—$CF_3$, —S-phenyl, and —S—Si—$(CH_3)_3$ in the presence of a catalyst.

The process of this invention may be carried out in either catalytic vapor or liquid phase. The process is preferably conducted at a temperature of from about 50° to about 600° C. The liquid phase process is preferably conducted in a solvent. The solvent may be any suitable solvent, preferably $H_2SO_4$ or a high boiling (bp 45° to 75° C. or higher) fluorocarbon solvent, such as hexafluorobenzene and the like.

The metal catalyst employed in the process may be employed alone or on a support material. The catalyst is preferably a metal salt such as salts of Cu, Hg, Pt, Pd, Co, Mn, Rh, Ni, V, TI, Ba, Cs, Ca K and Ge and mixtures thereof. Examples of suitable support materials include basic oxides such as MgO, BaO and CaO, $BaCO_3$, $CsNO_3$, Ba $(NO_3)_2$, activated carbon, basic alumina, and $ZrO_2$. When the metal salt is employed on a support material the metal salt will generally be employed in an amount of from about 2 to about 60 wt %, based on the total weight of the metal salt and support combined. Examples of suitable catalyst include $VO(acac)_2$, Pd/C, $Pd(acac)_2$ and $Co(acac)_2$. Preferably, a mixture of metal salts, such as Cu—Pt on a support such as activated carbon is employed to obtain higher selectivity of $CF_3I$ production.

To prevent or reduce catalyst deactivation and for iodine ($I_2$) economy it is preferred that the reaction be conducted in the presence of a source of a stoichiometric proportion of oxygen, such as air or $O_2$.

The reaction pathway for the process of this invention is believed to be as follows, as exemplified for the reactant $CF_3$—S—S—$CF_3$.

$CF_3$—S—S—$CF_3+I_2+2O_2\rightarrow 2CF_3I+2SO_2$

The invention is illustrated by, but not limited to, the following examples.

EXAMPLE 1

In a gas-phase process 20 SCCM (standard cubic centimeters) of $CF_3$—S—S—$CF_3$ and 20 SCCM of $I_2$ and 20 SCCM air are passed through a ½-inch (1.27 cm) reactor loaded with 50 cc of Pd/activated carbon catalyst at 350° C. in the presence of air to synthesize $CF_3I$. The products can be analyzed and identified by G C and GCMS.

EXAMPLES 2 TO 4

In reactions as described in Example 1, but when the reactant $CF_3$—S—S—$CF_3$ is replaced by CF3—SH, $CF_3$—S-phenyl, and $CF_3$—Si$(CH_3)_3$, respectively, $CF_3I$ is also produced.

EXAMPLES 5 TO 8

In a liquid phase process 5 gm of $CF_3$—S—S—$CF_3$ or $CF_3SH$, or $CF_3SPh$, or $CF_3$—Si$(CH_3)_3$, and 15 gm of Iodine are heated in an autoclave at 30–150° C. for 12 hrs in the presence of an inert solvent such as 100% $H_2SO_4$ solvent or a fluorocarbon solvent such as hexafluorobenzene. VO(acac)$_2$ is used as a catalyst. The conversion of the sulfur compounds to $CF_3I$ is around 80%.

The $CF_3I$ produced by the process of this invention is suitable for use as a refrigerant, either alone or combined with other refrigerants.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

What is claimed is:

1. A process for the production of $CF_3I$, the process comprising reacting a source of iodine selected from the group consisting of hydrogen iodide, iodine and iodine monochloride with a reactant selected from the group consisting of those of the formula:

$CF_3R$ where R is selected from the group consisting —SH, —S—S—$CF_3$, —S-phenyl, and —S—Si—$(CH_3)_3$ in the presence of a metal salt catalyst.

2. A process according to claim 1 wherein the reaction is conducted as a vapor phase reaction.

3. A process according to claim 1 wherein the reaction is conducted as a liquid phase reaction.

4. A process according to claim 1 wherein the reaction is conducted at a temperature of from about 50° to about 600° C.

5. A process according to claim 1 wherein the metal salt catalyst is selected from salts of Cu, Hg, Pt, Pd, Co, Mn, Rh, Ni, V, TI, Ba, Cs, ca, K and Ge and mixtures thereof.

6. A process according to claim 5 wherein the metal salt is on a support material.

7. A process according to claim 6 wherein the support material is selected from the group consisting of a basic oxide, $BaCO_3$, $CsNO_3$, $Ba(NO_3)_2$, activated carbon, basic alumina, and $ZrO_2$.

8. The process of claim 7 wherein the catalyst is-Pd/activated carbon.

9. The process according to claim 8 wherein the reaction is conducted in the presence of a source of oxygen.

10. A process according to claim 1 wherein the reaction is conducted in the presence of a source of oxygen and iodine is employed as a reactant.

* * * * *